(12) United States Patent
Wei et al.

(10) Patent No.: US 10,775,340 B2
(45) Date of Patent: Sep. 15, 2020

(54) APPARATUS AND ASSOCIATED METHODS FOR ANALYTE DETECTION

(71) Applicant: Nokia Technologies Oy, Espoo (FI)

(72) Inventors: Di Wei, Cambridge (GB); Michael Astley, Waterbeach (GB); Stefano Borini, Cambridge (GB); Jani Kivioja, Cambourne (GB)

(73) Assignee: Nokia Technologies Oy, Espoo (FI)

( * ) Notice: Subject to any disclaimer, the term of this patent is extended or adjusted under 35 U.S.C. 154(b) by 297 days.

(21) Appl. No.: 14/909,832

(22) PCT Filed: Jul. 25, 2014

(86) PCT No.: PCT/FI2014/050592
§ 371 (c)(1),
(2) Date: Feb. 3, 2016

(87) PCT Pub. No.: WO2015/018973
PCT Pub. Date: Feb. 12, 2015

(65) Prior Publication Data
US 2016/0187286 A1    Jun. 30, 2016

(30) Foreign Application Priority Data
Aug. 7, 2013   (GB) .................................. 1314149.4

(51) Int. Cl.
*G01N 27/407*   (2006.01)
*G01N 27/406*   (2006.01)
(Continued)

(52) U.S. Cl.
CPC ....... *G01N 27/4074* (2013.01); *G01N 27/333* (2013.01); *G01N 27/4065* (2013.01); *G01N 27/308* (2013.01); *G01N 33/0063* (2013.01)

(58) Field of Classification Search
CPC ............. G01N 27/4074; G01N 27/333; G01N 27/4065; G01N 27/308; G01N 33/0063;
(Continued)

(56) References Cited

U.S. PATENT DOCUMENTS

| | | |
|---|---|---|
| 4,522,690 A | 6/1985 | Venkatasetty |
| 6,001,239 A | 12/1999 | Douglas |

(Continued)

FOREIGN PATENT DOCUMENTS

| | | |
|---|---|---|
| CN | 1839309 A | 9/2006 |
| EP | 1751302 | 2/2007 |

(Continued)

OTHER PUBLICATIONS

M. Zhou, et al., Bioelectrochemical nterface Engineering: Toward the Fabrication of Electrochemical Biosensors, Biofuel Cells, and Self-Powered Logic Biosensors, Accounts of Chemical Research, vol. 44, No. 11, pp. 1232-1243 (2011) (Year: 2011).*

(Continued)

*Primary Examiner* — Maris R Kessel
(74) *Attorney, Agent, or Firm* — Harrington & Smith

(57) ABSTRACT

An apparatus comprising first and second electrodes (201, 202) separated by an electrolyte (203), the first and second electrodes (201, 202) configured to exhibit a potential difference therebetween on interaction of the first electrode (201) with an analyte, wherein the first electrode (201) is configured such that its electrical conductance and electrochemical potential are dependent upon the amount of analyte present, the electrical conductance and electrochemical potential of the first electrode (201) affecting the potential difference between the first and second electrodes (201, 202), and wherein the apparatus comprises respective first and second terminals (204, 205) configured for electrical connection to a readout circuit to enable determination of the presence and/or amount of analyte based on the potential difference.

16 Claims, 5 Drawing Sheets

(51) Int. Cl.
  *G01N 27/30* (2006.01)
  *G01N 33/00* (2006.01)
  *G01N 27/333* (2006.01)
(58) Field of Classification Search
  CPC .. H01M 2008/1095; H01M 8/00; H01M 8/02; H01M 8/0204; H01M 8/0206; H01M 8/0213; H01M 8/0223; H01M 8/023; H01M 8/0232; H01M 8/0234; H01M 8/0245
  See application file for complete search history.

(56) References Cited

U.S. PATENT DOCUMENTS

| | | | |
|---|---|---|---|
| 8,056,420 | B2 | 11/2011 | Chakrabartty et al. |
| 2003/0066519 | A1 | 4/2003 | Wachsman et al. |
| 2003/0141188 | A1 | 7/2003 | Imamura et al. |
| 2003/0205078 | A1 | 11/2003 | Hasei et al. |
| 2004/0101741 | A1* | 5/2004 | Minteer ............ C12N 11/08 429/401 |
| 2004/0245101 | A1 | 12/2004 | Willner et al. |
| 2006/0185979 | A1 | 8/2006 | Suda et al. |
| 2006/0207878 | A1 | 9/2006 | Myung |
| 2009/0117467 | A1 | 5/2009 | Zhamu et al. |
| 2010/0006431 | A1 | 1/2010 | Wallace et al. |
| 2010/0213082 | A1 | 8/2010 | Feldman et al. |
| 2010/0310907 | A1 | 12/2010 | Miller et al. |
| 2011/0014543 | A1 | 1/2011 | Taniguchi |
| 2011/0048943 | A1 | 3/2011 | Nemes |
| 2011/0111299 | A1 | 5/2011 | Liu et al. |
| 2011/0163314 | A1 | 7/2011 | Park et al. |
| 2012/0028127 | A1* | 2/2012 | Wei ............ B82Y 30/00 429/300 |
| 2012/0043858 | A1 | 2/2012 | Mahapatra et al. |
| 2012/0064409 | A1 | 3/2012 | Zhamu et al. |
| 2012/0067724 | A1 | 3/2012 | Kahn |
| 2012/0100402 | A1 | 4/2012 | Nesper et al. |
| 2012/0212242 | A1 | 8/2012 | Masel et al. |
| 2013/0045418 | A1 | 2/2013 | Oguni et al. |
| 2013/0052522 | A1 | 2/2013 | Inoue et al. |
| 2013/0062201 | A1 | 3/2013 | Jang et al. |
| 2013/0065120 | A1 | 3/2013 | Miwa |
| 2013/0162216 | A1 | 6/2013 | Zhamu et al. |
| 2014/0200538 | A1* | 7/2014 | Euliano ............ A61F 13/42 604/361 |

FOREIGN PATENT DOCUMENTS

| | | |
|---|---|---|
| EP | 2426487 | 3/2012 |
| WO | 9419685 | 9/1994 |
| WO | 2013049663 | 4/2013 |

OTHER PUBLICATIONS

Y. Sun, et al., Graphene/Polymer Composites for Energy Applications, Journal of Polymer Science, Part B: Polymer Physics, vol. 51, pp. 231-253, published online Dec. 10, 2012 (Year: 2012).*

L. Li, et al., A direct glucose alkaline fuel cell using MnO2ecarbon nanocomposite supported gold catalyst for anode glucose oxidation, Journal of Power Sources, vol. 221, pp. 1-5 (2013) (Year: 2013).*
Li et al., "Influence of water on the electronic structure of metal-supported graphene: Insights from van der Waals density functional theory", Physical Review B, vol. 85, 085425, Feb. 21, 2012, pp. 1-10.
Atabaki et al., "Graphene Composites as Anode Materials in Lithium-ion Batteries", Electronic Materials Letters, vol. 9, No. 2, 2013, pp. 133-153.
Li et al., "Supercapacitors Based on Nanostructured Carbon", Nano Energy, vol. 2, No. 2, 2013, pp. 159-173.
Choi et al., "Graphene for Energy Conversion and Storage in Fuel Cells and Supercapacitors", Nano Energy, vol. 1, No. 4, 2012, pp. 534-551.
Partial Supplementary European Search Report received for corresponding European Patent Application No. 14834267.8, dated Mar. 10, 2017, 06 pages.
Office action received for corresponding United Kingdom Patent Application No. 1314149.4, dated Oct. 23, 2017, 4 pages.
International Search Report and Written Opinion received for corresponding Patent Cooperation Treaty Application No. PCT/FI2014/050592 , dated Nov. 7, 2014, 17 pages.
Yao et al. 'The effect of ambient humidity on the electrical properties of graphene oxide films', in Nanoscale Research Letters 7:363, (2012), doi:10.1186/1556-276X-7-363.
Liu et al. 'Biological and chemical sensors based on graphene materials', in Chem. Soc. Rev. 41, p. 2283-2307, (2012), doi:10.1039/c1cs15270j.
Schedin et al. 'Detection of individual gas molecules adsorbed on graphene', in Nature Mater. 6, p. 652-655 (2007), doi:10.1038/nmat1967.
Kang et al. 'Glucose Oxidase—graphene—chitosan modified electrode for direct electrochemistry and glucose sensing', in Biosensors and Bioelectronics 25, p. 901-905 (2009), doi:10.1016/j.bios.2009.09.004.
Search Report received for corresponding GB Application No. 1314149.4, dated Jan. 30, 2014, 4 pages.
Office action received for corresponding Chinese Patent Application No. 201480055103.6, dated May 24, 2017, 6 pages of office action and no page of translation available.
Extended European Search Report received for corresponding European Patent Application No. 14834267.8, dated Jun. 1, 2017, 12 pages.
Yan et al., "Fabrication of Free-Standing, Electrochemically Active, and Biocompatible Graphene Oxide-Polyaniline and Graphene-Polyaniline Hybrid Papers", Applied Materials & Interfaces, vol. 2, No. 9, 2010, pp. 2521-2529.
Qiu et al., "Controllable Deposition of a Platinum Nanoparticle Ensemble on a Polyaniline/Graphene Hybrid as a Novel Electrode Material for Electrochemical Sensing", Chemistry European Journal, vol. 18, No. 25, 2012, pp. 7950-7959.
Inhwa Jung et al.: *Effect of Water Vapor on Electrical Properties of Individual Reduced Graphene Oxide Sheets*, Journal of Physical Chemistry C.

* cited by examiner

APPARATUS AND ASSOCIATED METHODS FOR ANALYTE DETECTION

RELATED APPLICATION

This application was originally filed as PCT Application No. PCT/FI2014/050592 filed Jul. 25, 2014 which claims priority benefit from GB Application No. 1314149.4, filed Aug. 7, 2013.

TECHNICAL FIELD

The present disclosure relates to the field of sensors, associated methods and apparatus, and in particular concerns an apparatus comprising first and second electrodes for use in determining the presence and/or amount of analyte in the environment in which the apparatus is located based on a measurement of the potential difference between the electrodes. Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

Electronic sensors typically need an independent power source to provide an excitation to the sensor and to power some form of display to the user. The power source is usually a separate battery. The need for an independent power source adversely affects miniaturization of the device, limits design freedom and increases the manufacturing costs. In addition, because sensors need to be able to monitor their surrounding environment continually, the lifetime of the power source tends to be relatively short.

One or more aspects/embodiments of the present disclosure may or may not address one or more of these issues.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising first and second electrodes separated by an electrolyte, the first and second electrodes configured to exhibit a potential difference therebetween on interaction of the first electrode with an analyte, wherein the first electrode is configured such that its electrical conductance and electrochemical potential are dependent upon the amount of analyte present, the electrical conductance and electrochemical potential of the first electrode affecting the potential difference between the first and second electrodes, and wherein the apparatus comprises respective first and second terminals configured for electrical connection to a readout circuit to enable determination of the presence and/or amount of analyte based on the potential difference.

The electrical conductance and electrochemical potential of the first electrode may affect the potential difference by influencing the internal resistance and electromotive force of the apparatus, respectively. The first electrode may be an anode and the second electrode may be a cathode.

The readout circuit may form part of the apparatus.

The readout circuit may be configured to measure the potential difference. The readout circuit may be configured to determine the presence and/or amount of analyte using the potential difference measurement. The readout circuit may be configured to indicate the presence and/or amount of analyte. The readout circuit may be configured to indicate the potential difference measurement to allow determination of the presence and/or amount of analyte. The indication may comprise a presentation or transmission of the respective data.

The readout circuit may be configured to generate a signal in response to the potential difference to allow determination of the presence and/or amount of analyte. The readout circuit may be configured such that the signal is correlated (e.g. proportional) to the magnitude of the potential difference. The readout circuit may be configured such that the signal is generated only when the potential difference exceeds a predetermined threshold. The readout circuit may comprise a switch configured to trigger generation of the signal when the predetermined threshold has been exceeded. The switch may comprise a metal-oxide-semiconductor field-effect transistor. The readout circuit may comprise a light emitting diode. The signal may comprise the emission of light by the light emitting diode.

The first electrode may comprise a graphene oxide film. The first electrode may comprise a metal mesh or layer of patterned metal on top of the graphene oxide film. The first electrode may comprise graphene oxide and a conducting polymer in the form of a composite material. The conducting polymer may comprise polyaniline. The graphene oxide may comprise one or more carboxyl, hydroxyl and/or epoxy groups. The graphene oxide may be partially reduced. The second electrode may comprise one or more of lithium oxide and manganese dioxide. The lithium oxide may comprise one or more of $LiMnO_4$, $LiCoO_2$ and $LiFePO_4$. The electrolyte may comprise one or more of polyvinylidene fluoride, polyacrylic, polyester and a polyethylene oxide derivative.

The analyte may comprise one or more of a chemical and biological species. The analyte may comprise one or more of a gas, liquid and vapour. The analyte may comprise water.

The apparatus may be one or more of an electronic device, a portable electronic device, a portable telecommunications device, a sensor, a battery, a capacitor, a battery-capacitor hybrid, and a module for any of the aforementioned devices. The sensor may be an environmental sensor such as a humidity sensor.

According to a further aspect, there is provided a method comprising determining the presence and/or amount of analyte using an apparatus and a readout circuit, the apparatus comprising first and second electrodes separated by an electrolyte, the first and second electrodes configured to exhibit a potential difference therebetween on interaction of the first electrode with an analyte, wherein the first electrode is configured such that its electrical conductance and electrochemical potential are dependent upon the amount of analyte present, the electrical conductance and electrochemical potential of the first electrode affecting the potential difference between the first and second electrodes, and wherein the apparatus comprises respective first and second terminals configured for electrical connection to the readout circuit to enable determination of the presence and/or amount of analyte based on the potential difference.

According to a further aspect, there is provided a method of making an apparatus for use in determining the presence and/or amount of analyte, the method comprising:

forming first and second electrodes, the first and second electrodes configured to exhibit a potential difference therebetween on interaction of the first electrode with an analyte, wherein the first electrode is configured such that its electrical conductance and electrochemical potential are dependent upon the amount of analyte present, the electrical conductance and electrochemical potential of the first electrode affecting the potential difference between the first and second electrodes;

providing an electrolyte between the first and second electrodes; and forming respective first and second terminals for electrical connection to a readout circuit to enable determination of the presence and/or amount of analyte based on the potential difference.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

DESCRIPTION OF SPECIFIC ASPECTS/EMBODIMENTS

As mentioned in the background section, the size, form factor, cost and energy efficiency of electronic sensors are adversely affected by their reliance on independent power sources. There will now be described an apparatus and associated methods that may or may not provide a solution to one or more of these issues.

Figure 1:
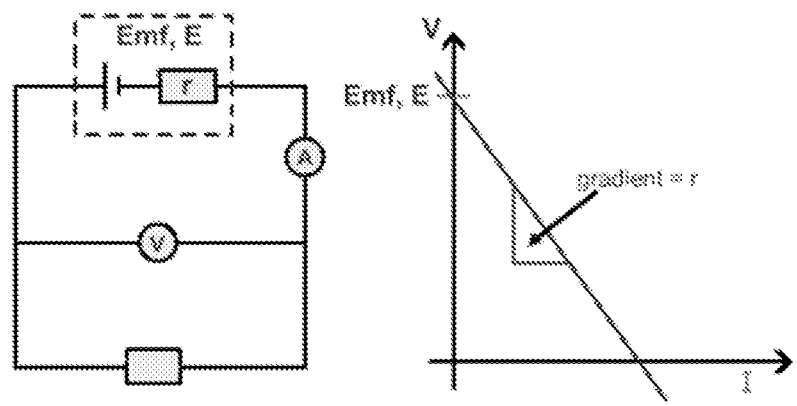
FIG. 1 shows a conventional battery and associated IN curve.

A battery may be modelled as an electromotive force in series with an internal resistance, as shown in FIG. 1. The potential difference (V) of a battery is related to its electromotive force (E) and internal resistance (r) by $$V = E - Ir \qquad \text{Equation 1}$$

where I is the current flowing round the circuit as a result of the potential difference.

Figure 2:
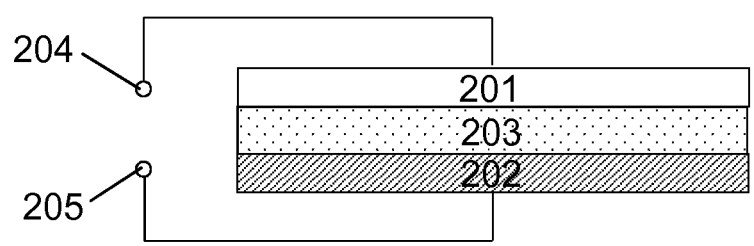
FIG. 2 shows an apparatus according to one embodiment of the present disclosure.

One embodiment of the present apparatus (illustrated schematically in FIG. 2) comprises first 201 and second 202 electrodes separated by an electrolyte 203, the first 201 and second 202 electrodes configured to exhibit a potential difference (V) therebetween on interaction of the first electrode 201 with an analyte. The first electrode 201 is configured such that its electrical conductance and electrochemical potential are dependent upon the amount of analyte present. Since the electrical conductance and electrochemical potential of the first electrode 201 influence the internal resistance (r) and electromotive force (E) of the apparatus, respectively, the presence of the analyte strongly affects the potential difference (V) between the first 201 and second 202 electrodes. In this way, the presence and/or amount of analyte can be determined based on the potential difference (V) of the apparatus. As shown in FIG. 2, the apparatus also comprises respective first 204 and second 205 terminals configured for electrical connection to a readout circuit (discussed in more detail below) to enable said determination.

Since the analyte creates the potential difference between the first 201 and second 202 electrodes, which in turn is used to sense the analyte, the present apparatus may be viewed as a self-powered sensor (or at least a module thereof). To enable this approach to work, the first electrode 201 should comprise a material whose electrical conductance and electrochemical potential vary with the amount of analyte present. The type of electrode material used, however, will depend on the specific analyte (i.e. the particular chemical or biological species) being detected and the environment in which the apparatus is used.

Figure 3:
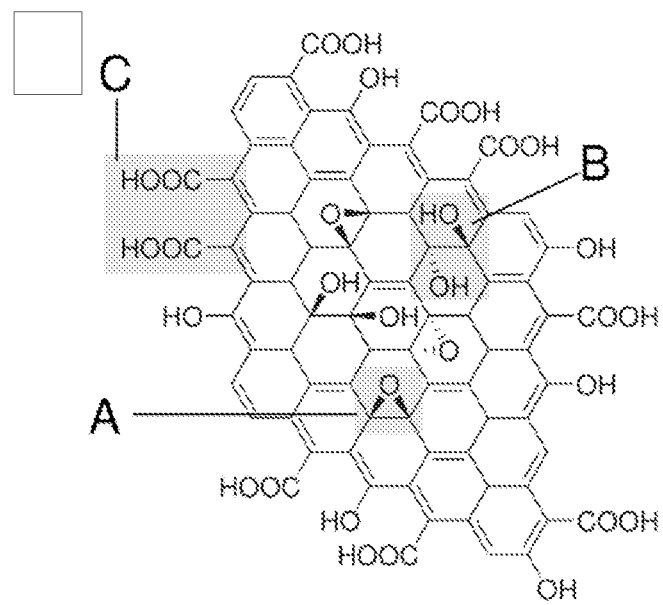
FIG. 3 shows the chemical structure of graphene oxide.

One example is graphene oxide for detecting water (in gaseous, liquid and/or vapour form) in the air, i.e. as a humidity sensor. Graphene oxide may be considered as graphene with one or more functional groups attached thereto, such as carboxyl (C), hydroxyl (B) and/or epoxy (A) groups as shown in FIG. 3. A battery which uses a thin graphene oxide film as the anode has an internal resistance (r) approximated by $$r = r_0 \exp(-H/H_0) \qquad \text{Equation 2}$$

where H is the relative humidity and $r_0$ and $H_0$ are constants which are dependent upon the anode's particular structure and geometry. The anode's conductance can be tailored to a specific application by varying the geometry of the electrode and incorporating other materials. For example, by depositing a metal mesh on top of the graphene oxide film, the internal resistance of the battery may be decreased by orders of magnitude due to the mesh bridging across discontinuities in the graphene oxide film. Alternatively, a layer of patterned metal may be deposited on top of the graphene oxide film, the resistance of which can be engineered by tailoring the metal pattern. Furthermore, if the conductivity of the electrode is intrinsically low, it may be increased using a conductive polymer (e.g. polyaniline) to form a graphene oxide polymer composite.

Figure 4:
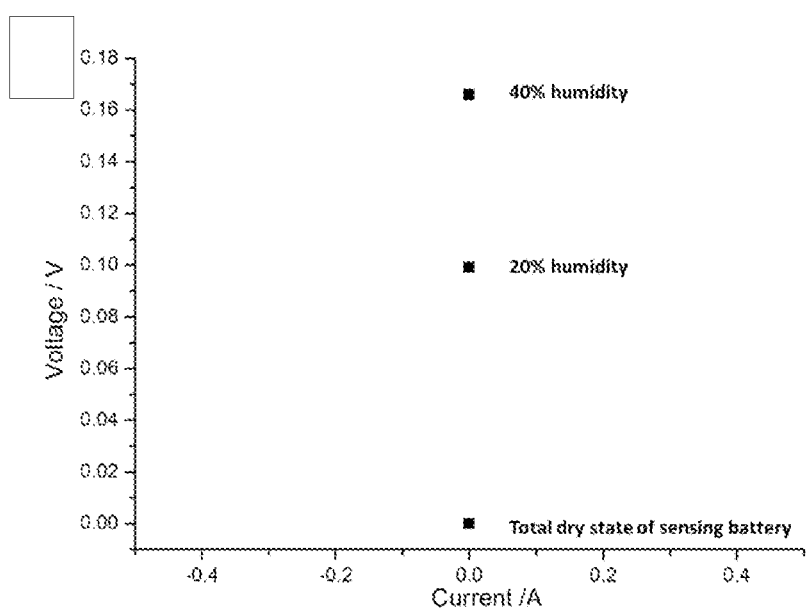
FIG. 4 shows open-circuit potential difference measurements for a graphene oxide-based battery at different humidity levels.

The electromotive force of a battery depends on the relative alignment of the Fermi energy between the anode and cathode. It has been shown that water has an influence on the electronic structure of metal-supported graphene with a shift in Fermi level (electrochemical potential) on the order of 100 meV. Such a shift becomes more severe when graphene includes one or more carboxyl, hydroxyl and/or epoxy groups. The electrochemical potential of graphene oxide therefore varies greatly with changes in water concentration. This can be seen in FIG. 4, which shows open-circuit voltage measurements for a graphene oxide-based battery at different humidity levels. In this example, the battery had a graphene oxide-coated anode, a polyester electrolyte and a $LiCoO_2$ cathode.

The change in output voltage (potential difference) of a graphene oxide-based battery with humidity is therefore caused not only by a change in the conductance of the graphene oxide, but also by a change in the electrochemical potential of the graphene oxide.

The first electrode material and analyte are not limited solely to graphene oxide and water, respectively. Other examples include 2D transition metal dichalcogenides (e.g. $MoS_2$) for sensing triethylamine; graphene for sensing ammonia and $NO_2$; functionalised graphene (e.g. graphene functionalised with enzymes) for sensing glucose; silver nanoparticles for sensing ammonia; and porous silicone for sensing ammonia.

Figure 5:
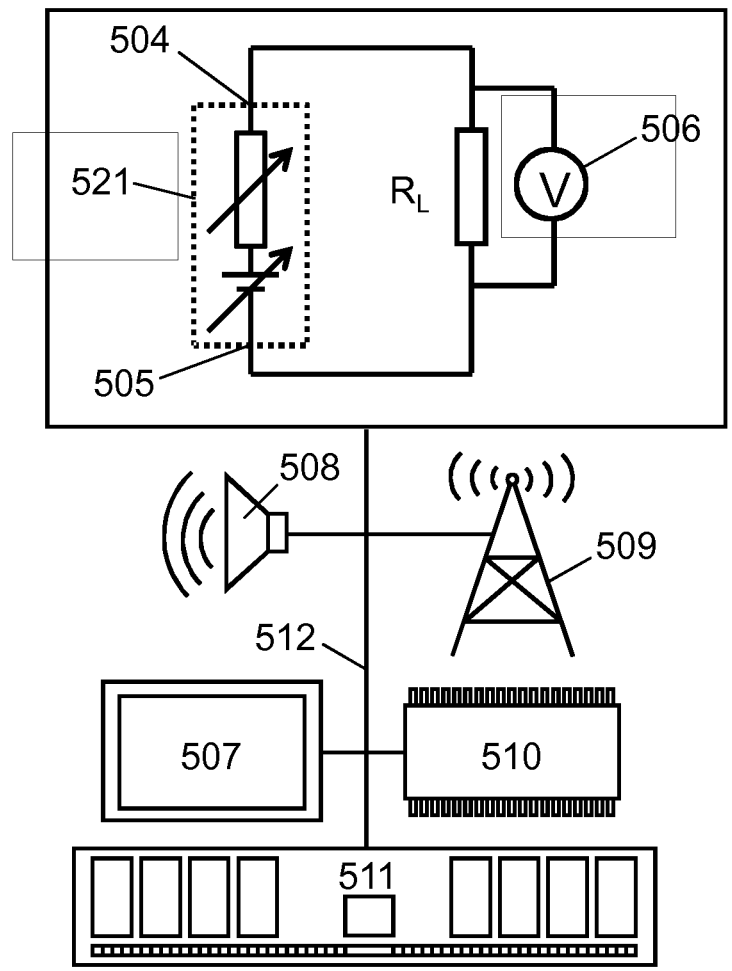
FIG. 5 shows an apparatus according to another embodiment of the present disclosure.

The readout circuit used to enable determination of the presence and/or amount of analyte may form part of the present apparatus. In some embodiments, the readout circuit may be configured to measure the potential difference. One example is shown in FIG. 5 in which the readout circuit comprises a voltmeter 506 connected across the first 504 and second 505 terminals. The apparatus of FIG. 2 is represented here as a power supply with variable output voltage and internal resistance (see dashed box 521). The readout circuit may also be configured to indicate the potential difference measurement to a user of the apparatus such that he/she can detect the presence of the analyte and quantify it based on this measurement. To achieve this, the apparatus/readout circuit may comprise an electronic display 507 and/or loudspeaker 508 for presenting the potential difference measurement to the user, and may further comprise a transmitter 509 (or transceiver) for transmitting the data to another device. The latter feature enables the user to monitor the environment from a remote location.

The apparatus/readout circuit may also comprise a processor 510 and storage medium 511 electrically connected to the other components by a data bus 512. The processor 510 is configured for general operation of the apparatus by providing signalling to, and receiving signalling from, the other components to manage their operation. The storage medium 511 is configured to store computer code configured to perform, control or enable operation of the apparatus. The storage medium 511 may also be configured to store settings for the other components. The processor 510 may access the storage medium 511 to retrieve the component settings in order to manage the operation of the other components. The processor 510 may be a microprocessor, including an Application Specific Integrated Circuit (ASIC). The storage medium 511 may be a temporary storage medium such as a volatile random access memory. On the other hand, the storage medium 511 may be a permanent storage medium such as a hard disk drive, a flash memory, or a non-volatile random access memory.

In another embodiment, the readout circuit may be configured to determine the presence and/or amount of analyte using the potential difference measurement and indicate the result to the user (with or without the potential difference measurement). This embodiment therefore provides the user with the end result without requiring him/her to derive it from the raw voltage data. In practice, this analysis would be performed by the processor 510 in combination with the storage medium 511. For example, the processor 510 may be configured to receive the potential difference measurement from the voltmeter 506 and compare this with predetermined calibration data (e.g. predetermined measurements of potential difference versus analyte concentration) from the storage medium 511 to determine the presence and/or amount of analyte.

Figure 6:
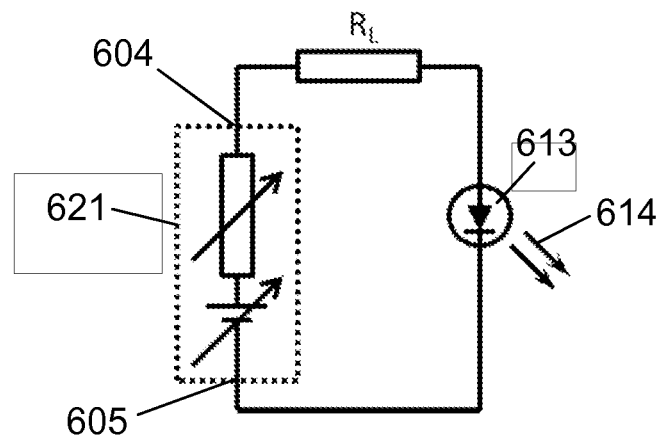
FIG. 6 shows an apparatus according to another embodiment of the present disclosure.

In other embodiments, the readout circuit may be configured to generate a signal in response to the potential difference to allow determination of the presence and/or amount of analyte. One example is shown in FIG. 6 in which the readout circuit comprises a light emitting diode (LED) 613 and the signal comprises the emission of light 614 by the LED 613. In this example, the amount of light 614 emitted is correlated to the magnitude of the potential difference. In this way, the user of the apparatus can determine how much analyte is present from the brightness of the LED 613. A downside to this configuration, however, is that it may be difficult for the user to distinguish between different brightness's to enable accurate quantification. Furthermore, in the configuration of FIG. 6, the LED 613 will continue to draw a current (albeit a small one) even when the humidity is low (i.e. in the "off" state when the internal resistance of the apparatus is high), thus reducing the efficiency of the sensor apparatus.

Figure 7:
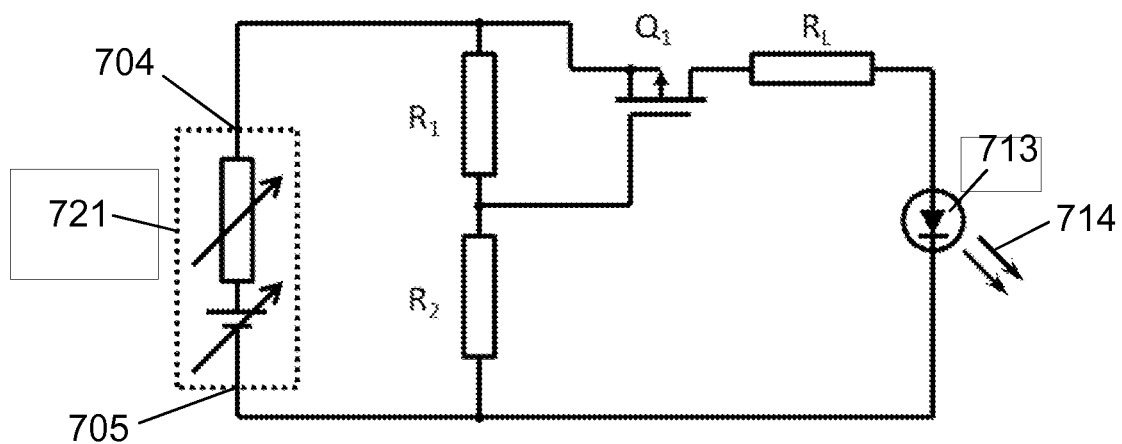
FIG. 7 shows an apparatus according to another embodiment of the present disclosure.

FIG. 7 shows another embodiment in which the readout circuit is configured to generate a signal only when the potential difference exceeds a predetermined threshold. As before, the signal is the light 714 produced by an LED 713 in response to the potential difference, but the readout circuit now comprises a switch $Q_1$ (in this example, a metal-oxide-semiconductor field-effect transistor (MOSFET)) configured to trigger generation of the signal when the predetermined threshold has been exceeded. The MOSFET $Q_1$ will only open when the source-drain voltage is greater than the threshold voltage of the transistor. The source-drain voltage V is given by $$V = \frac{V_+}{\left(1 + \frac{R_2}{R_1}\right)} \qquad \text{Equation 3}$$

where $V_+$ is the voltage at the positive terminal 704 of the apparatus. This means that the LED 713 has a low current draw when the apparatus is in the "off" state and a sharp on/off response. Since the apparatus (including the readout circuit) is only active when then analyte is present, its energy efficiency is high resulting in a greater lifetime. The obvious downside of this embodiment, however, is the fact that the output from the readout circuit is qualitative rather than quantitative (i.e. the user can determine if the analyte is present, but not how much of the analyte is present).

In each of the examples described above, the apparatus may be one or more of an electronic device, a portable electronic device, a portable telecommunications device, a sensor, a battery, a capacitor, a battery-capacitor hybrid, and a module for any of the aforementioned devices.

Figure 8:
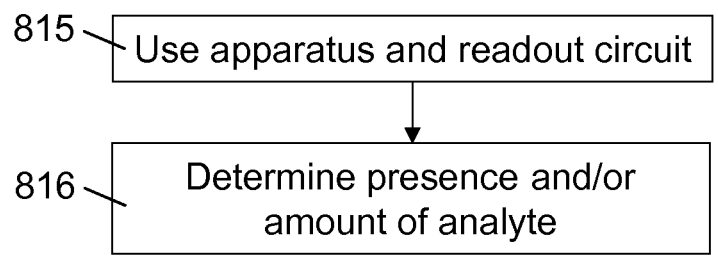
FIG. 8 shows the main steps of a method of determining the presence and/or amount of analyte using the apparatus described herein.

The main steps 815-816 of a method of using the apparatus in determining the presence and/or amount of analyte are shown schematically in FIG. 8. Similarly, the main steps 917-919 of a method of making the apparatus are shown schematically in FIG. 9.

A number of different fabrication processes may be used to form the present apparatus. In particular, the whole device may be made using screen printing, gravure printing, ink-jet printing or roll-to-roll printing, thereby lowering its manufacturing cost significantly. In this scenario, any components of the associated readout circuit which cannot be directly printed may be bonded to the apparatus using a conductive epoxy.

The first electrode may comprise a graphene oxide (or partially reduced graphene oxide) film with or without a metal mesh or layer of patterned metal deposited thereon. Alternatively, the first electrode may comprise a composite material comprising graphene oxide and a conducting polymer (e.g. polyaniline). The graphene oxide may comprise one or more carboxyl, hydroxyl and/or epoxy groups. The second electrode, on the other hand, may comprise one or more of lithium oxide (e.g. $LiMnO_4$, $LiCoO_2$ or $LiFePO_4$) and manganese dioxide, whilst the electrolyte is preferably a solid or gel electrolyte comprising one or more of polyvinylidene fluoride, polyacrylic, polyester and a polyethylene oxide derivative.

Figure 10:
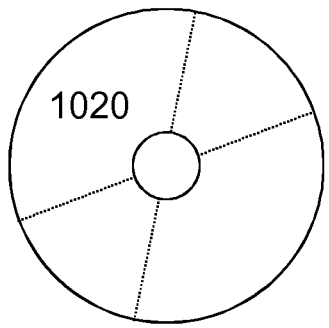
FIG. 10 shows a computer-readable medium comprising a computer program configured to perform, control or enable one or more of the method steps of FIG. 8 or 9.

FIG. 10 illustrates schematically a computer/processor readable medium 1020 providing a computer program according to one embodiment. In this example, the computer/processor readable medium 1010 is a disc such as a digital versatile disc (DVD) or a compact disc (CD). In other embodiments, the computer/processor readable medium 1020 may be any medium that has been programmed in such a way as to carry out an inventive function. The computer/processor readable medium 1020 may be a removable memory device such as a memory stick or memory card (SD, mini SD, micro SD or nano SD).

Figure 9:
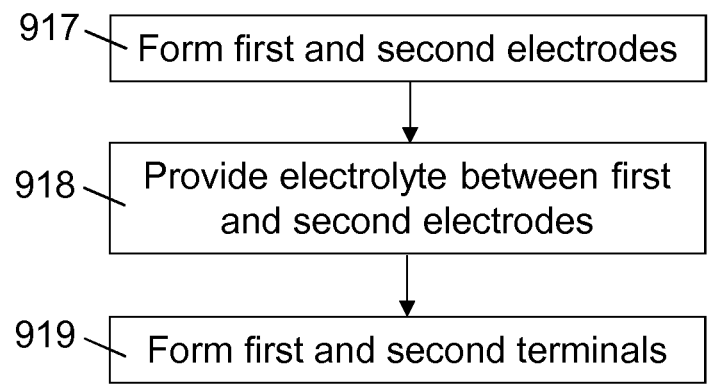
FIG. 9 shows the main steps of a method of making the apparatus described herein.

The computer program may comprise computer code configured to perform, control or enable one or more of the method steps 815-816, 917-917 of FIG. 8 or 9. In particular, the computer program may be configured to measure the potential difference between the terminals of the apparatus, and may also be configured to determine the presence and/or amount of analyte based on the measured potential difference. Additionally or alternatively, the computer program may be configured to control the above-mentioned fabrication processes to form/assemble the apparatus.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising:
    first and second electrodes separated by an electrolyte, the first and second electrodes configured to exhibit a potential difference therebetween on interaction of the first electrode with an analyte; and
    a readout circuit,
    wherein the first electrode comprises a graphene oxide film and a metal mesh or layer of patterned metal on top of the graphene oxide film and is configured such that electrical conductance and electrochemical potential of the first electrode are dependent upon an amount of the analyte present, the electrical conductance and electrochemical potential of the first electrode affecting the potential difference between the first and second electrodes,
    wherein the apparatus comprises respective first and second terminals configured for electrical connection to the readout circuit powered by the potential difference as affected by the analyte, and
    wherein the readout circuit is configured to determine one or more of presence and amount of the analyte based on the potential difference.

2. The apparatus of claim 1, wherein the determination is based on a measure of the potential difference.

3. The apparatus of claim 2, wherein the readout circuit indicates the one or more of presence and amount of analyte using the potential difference measurement.

4. The apparatus of claim 1, wherein the readout circuit is configured to generate a signal in response to the determination.

5. The apparatus of claim 4, wherein the readout circuit is configured such that the signal is correlated to the magnitude of the potential difference.

6. The apparatus of claim 4, wherein the readout circuit is configured such that the signal is generated only when the potential difference exceeds a predetermined threshold.

7. The apparatus of claim 6, wherein the readout circuit comprises a switch configured to trigger generation of the signal when the predetermined threshold has been exceeded.

8. The apparatus of claim 4, wherein the readout circuit comprises a light emitting diode and the signal comprises emission of light by the light emitting diode.

9. The apparatus of claim 1, wherein the first electrode comprises graphene oxide and a conducting polymer in the form of a composite material.

10. The apparatus of claim 1, wherein the second electrode comprises one or more of lithium oxide and manganese dioxide.

11. The apparatus of claim 1, wherein the electrolyte comprises one or more of polyvinylidene fluoride, polyacrylic, polyester and a polyethylene oxide derivative.

12. The apparatus of claim 1, wherein the analyte comprises one or more of a chemical and biological species.

13. The apparatus of claim 1, wherein the analyte comprises water.

14. The apparatus of claim 1, wherein the apparatus is one or more of an electronic device, a portable electronic device, a portable telecommunications device, a sensor, a battery, a capacitor, a battery-capacitor hybrid, and a module for any of the aforementioned devices.

15. A method comprising: determining the presence and/or amount of analyte using an apparatus and a readout circuit, the apparatus comprising first and second electrodes separated by an electrolyte, the first and second electrodes exhibiting a potential difference therebetween on interaction of the first electrode with an analyte, wherein the first electrode comprises a graphene oxide film and a metal mesh or layer of patterned metal on top of the graphene oxide film such that electrical conductance and electrochemical potential of the first electrode are dependent upon an amount of the analyte present, the electrical conductance and electrochemical potential of the first electrode affecting the potential difference between the first and second electrodes, and wherein the apparatus comprises respective first and second terminals electrically connecting the first and second terminals to a readout circuit powered by the potential difference as affected by the analyte and determining one or more of presence and amount of the analyte based on the potential difference.

16. A method of making an apparatus for use in determining the presence and/or amount of analyte, the method comprising:
    forming first and second electrodes, the first and second electrodes exhibiting a potential difference therebetween on interaction of the first electrode with an analyte, wherein the first electrode comprises a graphene oxide film and a metal mesh or layer of patterned metal on top of the graphene oxide film such that electrical conductance and electrochemical potential of the first electrode are dependent upon the amount of analyte present, the electrical conductance and electrochemical potential of the first electrode affecting the potential difference between the first and second electrodes;
    providing an electrolyte between the first and second electrodes; and
    forming respective first and second terminals for electrical connection to a readout circuit powered by the potential difference as affected by the analyte and determining one or more of presence and amount of the analyte based on the potential difference.

* * * * *